United States Patent [19]

Vierling et al.

[11] Patent Number: 6,096,944

[45] Date of Patent: Aug. 1, 2000

[54] METHODS FOR CONFERRING BROAD-BASED SOYBEAN CYST NEMATODE RESISTANCE TO A SOYBEAN LINE

[75] Inventors: Richard A. Vierling, Lafayette; Jamal Faghihi, West Lafayette; Virginia R. Ferris, West Lafayette; John M. Ferris, West Lafayette, all of Ind.

[73] Assignee: Purdue Research Foundation, West Lafayette, Ind.

[21] Appl. No.: 08/764,857

[22] Filed: Dec. 13, 1996

Related U.S. Application Data

[60] Provisional application No. 60/008,677, Dec. 15, 1995, and provisional application No. 60/013,597, Dec. 18, 1995.

[51] Int. Cl.$^7$ .............................. A01H 1/04; A01H 5/00; A01H 5/10; C12Q 1/68
[52] U.S. Cl. .................... 800/265; 800/267; 800/298; 800/312; 435/6
[58] Field of Search .................... 800/200, 205, 800/DIG. 26, 265, 260, 266, 267, 298, 301, 312; 47/58, DIG. 1; 435/6, 172.3, 172.1; 536/24.3, 23.1

[56] References Cited

U.S. PATENT DOCUMENTS

| | | | |
|---|---|---|---|
| 5,084,082 | 1/1992 | Sebastian | 71/90 |
| 5,264,210 | 11/1993 | Novitski et al. | 47/58 |
| 5,270,448 | 12/1993 | Payne | 530/350 |
| 5,332,408 | 7/1994 | Mets et al. | 47/58 |
| 5,385,835 | 1/1995 | Helentjaris et al. | 435/172.3 |
| 5,437,697 | 8/1995 | Sebastian et al. | 47/58 |
| 5,491,081 | 2/1996 | Webb | 435/172.3 |

FOREIGN PATENT DOCUMENTS 0 568 027 A1   3/1993   European Pat. Off. ....... A01N 63/00

OTHER PUBLICATIONS

Shoemaker et al. Crop Science 35:436–446, 1995.

Young et al. Induced Mutations and Molecular Techniques for Crop Improvement, Proceedings of a Symposium, Vienna, 1995.

Tanksley et al. RFLP mapping in plant breeding: new tools for an old science. Bio/technology. vol. 7 pp. 257–264, 1989.

Mark Walton, *Molecular Markers: Which Ones To Use?*, Seed World, Jul., 1993, pp. 22–26.

J.M. Wiesemann, B.F. Matthews and T.E. Devine, *Molecular Markers Located Proximal to the Soybean Cyst Nematode Resistance Gene*, Rhg4, Theor. Appl. Genet., 1992, 85:136–138.

S. Boutin, H. Ansari, V. Concibido, R. Denny, J. Orf, N. Young, *RFLP Analysis of Cyst Nematode Resistance in Soybeans*, 1992, Soybean Genetics Newsletter, 19:123–127.

V. Concibido, R. Denny, S. Boutin, R. Hautea, J. Orf, N. Young, *RFLP Mapping of Cyst Nematode Resistance Genes in Soybeans*, 1993, Soybean Genetics Newsletter, 20:136–139.

A. P. Rao–Arelli, Sam C. Anand, and J. Allen Wrather, *Soybean Resistance to Soybean Cyst Neamtode Race 3 Is Conditioned by an Additional Dominant Gene*, Crop Science, 1992, 32:862–864.

S.C. Anand, J.A. Wrather, and C.R. Shumway, *Soybean Genotypes with Resistance to Races of Soybean Cyst Nematode*, Crop Science, Nov.–Dec. 1985, 25:1073–1075.

Baltazar Baltazar M., Dr. Levi Mansur, *Identification of Restriction Fragment Length Polymorphisms (RFLP's) to Map Soybean Cyst Nematode Resistance Genes in Soybean*, Soybean Genetics Newsletter, 1992, 19:120–122.

Arnold I. Matson and Leonard F. Williams, *Evidence of a Fourth Gene for Resistance to the Soybean Cyst Nematode*, Crop Science, 1965, 5:477.

Celia A. May, and Jon H. Wetton, *DNA Finferprinting by Specific Priming of Concatenated Oligonucleotides*, Nucleic Acids Research, 1991, 19, 6:4557.

S.C. Anand, and Karen M. Gallo, *Identification of Additional Soybean Germ Plasm with Resistance to Race 3 of the Soybean Cyst Nematode*, Plant Disease, 1984, 68:593–595.

G.O. Myers, and S.C. Anand, *Inheritance of Resistance and Genetic Relationships Among Soybean Plant Introductions to Races of Soybean Cyst Nematode*, Euphytica, 1991, 55:197–201.

G.O. Myers, S.C. Anand, and A.P. Rao–Arelli, *Resistance to Heterodera Glycines in Soybean PI 437654*, 1989, 1230–1243.

V.C. Concibido, R.L. Denny, S.R. Boutin, R. Hautea, J.H. Orf, and N.D. Young, *DNA Marker Analysis of Loci Underlying Resistance to Soybean Cyst Nematode (Heterodera Glycines Ichinohe)*, Crop Science, 1994, 34:240–246.

B.E. Caldwell, C.A. Brim, and J.P. Ross, *Inheritance of Resistance of Soybeans to the Cyst Nematode*, Heterodera Glysines, Agronomy Journal, 1960, 52:635–636.

R.W. Michelmore, I. Paran, and R.V. Kesseli, *Identification of Markers Linked to Disease–Resistance Genes by Bulked Segregant Analysis: A Rapid Method to Detect Markers in Specific Genomic Regions by Using Segregating Populations*, Proc. Natl. Acad. Science USA, 1991, 88:9828–9832.

(List continued on next page.)

*Primary Examiner*—Gary Benzion
*Assistant Examiner*—Melissa L. Kimball
*Attorney, Agent, or Firm*—Woodard, Emhardt, Naughton Moriarty & McNett

[57] ABSTRACT

Described are recombinant soybean plants and plant lines, and methods for producing the same, which have desired characteristics derived from one or more soybean lines and which are soybean cyst nematode-resistant, this resistance having been introgressed by marker-assisted selection. The soybean cyst nematode resistance is advantageously introgressed using inventive methods with minimal linkage drag and, as such, resulting plants do not exhibit undesirable characteristics heretofore associated with plants and plant lines having resistance to soybean cyst nematodes.

31 Claims, 3 Drawing Sheets

OTHER PUBLICATIONS

A.P. Rao–Arelli and S.C. Anand, *Genetic Relationships among Soybean Introductions for Resistance to Race 3 of Soybean Cyst Nematode*, Crop Science, 1988, 28:650–652.

Weidong Li, S.C. Anand, and K. W. Matson, *Linkage for Resistance to Race 5 and Race 3 of the Soybean Cyst Nematode (Heterodera Glycines) in the Cross PI 4376541x Tracy M*, Soybean Genetics Newsletter, 1989, 16:165–167.

N.M. Cowen, *The Use of Replicated Progenies in Marker–based mapping of OTL's*, Theor. Appl. Genet., 1988, 75:857–862.

J. Faghihi, R.A. Vierling, J.M. Halbrendt, V.R. Ferris, and J.M. Ferris, *Resistance Genes in a 'Williams 82' ×'Hartwig' Soybean Cross to an Inbred Line of Heterodera Glycines*, Journal of Nematology, 1995, 27(3):418–421.

R. Mahalingram, and H.T. Skorupska, *DNA Markers for Resistance to Heterodera Glycines I. Race 3 in Soybean Cultivar Peking*, Breeding Science, 1995, 45:435–443.

Walter R. Fehr, *Breeding Methods for Cultivar Development*, J.R. Wilcox (ed.), Soybeans: Improvement, Production, and Uses 2d ed., 1987, 249–292.

METHODS FOR CONFERRING BROAD-BASED SOYBEAN CYST NEMATODE RESISTANCE TO A SOYBEAN LINE

REFERENCE TO RELATED APPLICATIONS

This application claims priority upon U.S. patent application Ser. No. 60/008,677 filed Dec. 15, 1995, and U.S. patent Ser. No. 60/013,597 filed Dec. 18, 1995, each of which is hereby incorporated by reference in its entirety.

BACKGROUND OF THE INVENTION

1. Field of the Invention

The present invention relates to the field of plant breeding, specifically to methods of soybean breeding and the resulting soybean plants and soybean lines. More particularly, the invention relates to soybean cyst nematode-resistant soybean lines and methods of breeding same, the methods involving molecular marker analysis.

2. Discussion of Related Art

Soybeans are a major cash crop and investment commodity in North America and elsewhere. Soybean oil is one of the most widely used edible oils, and soybeans are used worldwide both in animal feed and in human food production. The soybean cake, or meal, that remains after processing the beans for oil, is a high-protein foodstuff used extensively in livestock and poultry rations. It is an excellent protein with respect to most of the essential amino acids and also a good source of vitamins of the B-complex.

Nematodes are small wormlike animals, many of which are plant, animal or human parasites which cause a variety of diseases. Plant pathogenic nematodes are a major agricultural problem causing significant crop and yield losses. Plant tissue, particularly root tissue, is damaged by nematode feeding. Such feeding can cause mechanical tissue damage and the accompanying injection of nematode enzymes can cause further tissue disintegration. Nematode infections of roots result in root galls, and distortions in root growth. Similar symptoms accompany nematode infections of other parts of the plants.

Nematode infection can also be accompanied by bacterial or fungal infection. In such plant-disease complexes, damage caused by nematodes can lead to enhanced severity of bacterial or fungal infection. In addition, several nematodes are vectors for plant pathogenic viruses.

The soybean cyst nematode, Heteroderaglycines, was apparently first identified on soybeans in the United States in 1954 at Castle Hayne, N.C. Since its discovery the soybean cyst nematode ("SCN") has been recognized as one of the most destructive pests in soybean. It has been reported in nearly all states in which soybeans are grown, and it causes major production problems in several states, being particularly destructive in the Midwestern states.

Although the use of nematocides is effective in reducing the population level of the nematode, nematocide use is both uneconomical and potentially environmentally unsound as a control measure in soybean production. Neither is crop rotation a practical means of nematode control, because rotation with a SCN-resistant crop for at least two years is necessary for reducing soybean losses and there currently exist no known SCN-resistant soybean plant lines which are commercially satisfactory. It has long been felt by soybean breeders that use of commercially satisfactory SCN-resistant varieties would be the most practical control measure. Therefore, there exists a great need in the relevant art for soybean plants and plant lines which are commercially satisfactory and are resistant to soybean cyst nematodes.

Screening of soybean germplasm for resistance to SCNs was begun soon after the discovery of the nematode in the United States. Although various soybean lines have proven resistant to various races of soybean cyst nematode, the plant introduction PI437654 is the only soybean line which has been shown to have resistance to all known SCN races (3, 1, 2, 5, 14, 6 and 9). However, a disadvantage of PI437654 is that its physical characteristics include a black seed coat, poor standability, seed shattering, and low yield, making it commercially unsatisfactory and making desirable the introgression of its SCN resistance into elite germplasm with a minimum of linkage drag. Conventional breeding with PI437654 produced the variety "Hartwig", which is more adapted to cultivation and can be used as a source of SCN resistance in soybean breeding; however, Hartwig retains and transfers the above-mentioned poor physical characteristics. Prior to the present invention, soybean breeders have been unable to selectively introgress SCN resistance without these poor physical characteristics.

Resistance to SCN has been shown to be multigenic and quantitative in soybean, although complete resistance can be scored qualitatively. It has previously been estimated that PI437654 has three genes required for complete resistance to race-3, four genes for race-5, and three genes for race-14. The multiple genes and SCN races involved contribute to the difficulty breeders have in developing soybean varieties having SCN resistance.

When considering the development of improved plant lines, a great deal of emphasis is usually placed on the strategy of introducing characteristics into plants via genetic engineering techniques. While there is excitement over advances in plant genetic engineering, the prospects for the general use of these techniques for plant improvement are tempered by the realization that very few genes corresponding to plant traits of interest have been identified. The use of direct gene transfer in manipulating these traits, of course, is therefore difficult due to problems in pinpointing and then cloning those individual loci which contribute predominantly to the expression of the trait.

Alternatively, much attention is being given to selective breeding techniques for introgressing one or more desired traits from one soybean plant line into another plant line having other desired traits. A procedure that has been used by plant breeders to increase efficiency in the testing of traits which are difficult or expensive to evaluate is the use of indirect selection criteria. One indirect selection criterion, for example, might be an easily recognized morphological characteristic of the plant which is either genetically linked to the desired trait or perhaps a component of the desired trait, e.g., the association between leaf size and seed size in beans.

Agronomically important traits such as, for example, plant yield, height, maturity, fruit and grain characteristics, and nematode resistance are all attractive targets for manipulation in plant improvement programs, but these traits often have very low heritabilities. Heritability is the proportion of observed variation in a particular trait that can be attributed to inherited genetic factors in contrast to environmental ones and, therefore, is important to the efficiency of the selection process. Influencing heritability of such traits, sometimes termed "quantitative" traits, is difficult, however, because expression of a number of different gene products generally influences the phenotype. Quantitative traits are thus often characterized by continuous rather than discreet distribution of phenotypic expression. There is currently a poor understanding of how single genes influence the expression of complex traits and, in conventional plant breeding programs, selection for inheritance of quantitative traits is difficult due to the unrecognized genetic basis of the trait. Determination of genotypic information from phenotypic values is further imprecise because evaluation of the trait may frequently be confounded by environmental effects.

A method of introgressing multigenic quantitative traits into wild germ plasm has been described by which the role of individual plant genes in quantitative trait expression may be identified and characterized. This method involves the determination of genetic markers closely linked to important genes, and the indirect selection for favorable alleles based upon the presence of the specific markers. This method allows selection to be accomplished more efficiently than direct phenotypic selection.

A class of plant molecular markers which has gained widespread acceptance is based upon restriction fragment length polymorphisms ("RFLP"s). Generally, RFLPs are differences observed between genotypes in the fragment lengths of restriction endonuclease-digested DNA. RFLPs occur as a result of base pair or positional changes in the restriction enzyme recognition sites which flank a chromosomal location and can be detected by hybridization of labelled DNA clones containing sequences that are homologous to a portion of the chromosomal fragment. Hybridization with a unique cloned sequence can permit the identification of a specific chromosomal region, or locus.

This technology conventionally employs cloned DNA fragments to detect differences between individuals at the DNA sequence level. When genomic DNAs from two genetically distinct individuals are digested with a restriction enzyme, electrophoresed and probed with a labelled DNA clone, polymorphisms in the hybridization patterns sometimes result due to sequence differences between the individuals. The term "restriction fragment length polymorphism" has been coined to describe this variation.

Differences in fragment lengths which are revealed, for example, by agarose gel electrophoresis, function as alleles of the RFLP. Thus, RFLPs can serve as genetic markers in a manner analogous to conventional morphological or isozyme markers. Unlike most genetic markers, however, they are not the products of transcription and translation. Additionally, RFLPs possess certain additional advantages over previously available genetic markers. First, RFLPs reflect existing differences between genetically distinct individuals. The potential number of RFLPs for all practical purposes is thus unlimited, as digestion of the genomic DNA of any higher eukaryote with a six base recognition enzyme will generate more than a million fragments, many of which can be polymorphic. Additionally, over one hundred different restriction enzymes have now been described, each of which may generate a new and different set of fragments.

RFLP markers rarely possess detectable phenotype effects of their own, so they can be utilized in economic lines without detriment and many can be evaluated at one time without the pleiotropic effects often seen with phenotypic markers. Evaluation can be performed on small amounts of DNA obtained from plant tissue at virtually any stage of plant development from seeds, to roots, to shoots, to fruits, or even with tissue culture material. Evaluation of RFLPs is not affected by environmental factors and greenhouse-grown plants will not differ from field-grown plants when tested. Finally, the evaluation of RFLPs reveals the exact genotype, so the heterozygous state can be differentiated from the homozygous condition at any chromosomal location.

Numerous direct applications of RFLP technology to facilitate plant breeding programs have been suggested. Because of the large numbers of RFLP markers available in a population of interest, one of the more important applications of RFLPs is as markers linked to genes affecting the expression of quantitatively inherited traits. A prerequisite for the use of RFLPs as indirect selection criteria is the identification of RFLPs closely linked to the genomic loci affecting expression of the trait of interest. Such genomic loci are commonly referred to as quantitative trait loci ("QTL's).

The introgression of quantitative traits from one germplasm to another conventionally involves the identification of favorable genotypes in a segregating generation followed by repeated backcrossing to commercially acceptable cultivars. This procedure is feasible for simply inherited quantitative traits, but as the number of genes controlling a trait increases, screening the number of F2 segregants required to identify at least one individual which represents the ideal (homozygous) genotype quickly becomes prohibitive. For example, with one gene and two alleles of equal frequency, the probability of recovering a desirable genotype on the F2 generation is ¼. However, if the number of genes is increased to 5 or 10, the probability of recovering an ideal genotype in the F2 population is reduced to approximately one in one thousand and one in one million, respectively. Thus, to identify desirable segregants, one must either reduce the number of segregants needed or have available very efficient screening procedures.

One described method of RFLP research involves crossing a plant source (designated $P_1$) having a desired multigenic trait, for example, SCN resistance, with a second plant (designated $P_2$) having essentially or substantially opposite characteristics, that is, SCN susceptibility. Heterozygous plants from the F1 population are selfed to create a segregating (F2) plant population which exhibits a gradient with respect to the degree of expression of the multigenic or quantitative trait of interest, e.g., SCN resistance.

Quantitative values for the trait of interest (SCN resistance) are determined and assigned to each individual parent plant, F1 population plant, and F2 segregating plant and a genomic DNA sample from each plant is prepared for Southern blotting. Following preparation for a Southern blot, an RFLP probe is randomly chosen or selected from an RFLP genetic linkage map and hybridized to create the blot. Additional Southern blots are constructed using other RFLP probes, and the degree of association between the trait of interest and each particular RFLP is determined. Additionally, in a multigenic system such as SCN resistance, the relative importance of each correlating RFLP can be determined. Particular values can be assigned to those RFLPs and utilized in a mathematical model to assist in predicting the degree of trait expression in a particular plant. In this manner, the RFLP marker(s) having the strongest association with the trait of interest can be determined and utilized, for example, in a breeding program to select plants having SCN resistance.

It is of particular importance, both to the soybean breeder and to farmers who grow and sell soybeans as a cash crop, to identify, through genetic mapping, QTLs associated with resistance to the various SCN races and to identify markers associated thereto which may be used to introgress SCN resistance with a minimal amount of linkage drag. Knowing these superior markers, soybean breeders will be better able to breed SCN resistant soybeans which also possess the other genotypic and phenotypic characteristics desired for commercial soybean plant lines. Superior markers and plants and plant lines developed using the same are provided by the present invention. Also provided are improved methods for identifying molecular markers linked to SCN resistance QTLs.

SUMMARY OF THE INVENTION

Briefly describing one aspect of the present invention, there is provided a recombinant soybean cyst nematode-resistant soybean plant line derived from selective breeding, this recombinant plant line having genomic DNA from two plant lines, the first plant line being soybean cyst nematode-resistant, and the second plant line being non-resistant or less resistant to soybean cyst nematodes ("SCN"s). The recombinant plants and plant lines of the present invention derive SCN resistance from the first plant line with minimal linkage drag and, thus, derive desired characteristics from the second plant line. This is accomplished according to inventive methods wherein selection of plants for breeding is based upon the presence of one or more molecular markers which the present inventors have shown to be linked to SCN resistance genomic loci, namely, A006, A567, A487, A112, A096-A, A486 and B039.

According to another aspect of the present invention, there are provided methods for mapping genomic loci associated with SCN resistance by identifying molecular markers linked thereto. In accordance with the invention, this method includes the use of restriction fragment length polymorphism analysis for genetic screening and the use of inbred soybean cyst nematode introduction for phenotypic screening.

In another aspect of the present invention, there are provided methods for producing recombinant SCN-resistant soybean plant lines by introgressing SCN resistance into a non-resistant or less resistant soybean line using marker-assisted selection. This selection comprises screening individual plants for the presence of one or more of the molecular markers described herein, and propagating these plants by, for example, single seed descent or backcrossing with, for example, plants from a non-resistant or less resistant parental soybean line.

The present inventors have successfully identified molecular markers associated with SCN resistance and, using these markers, have developed a soybean plant line which exhibits SCN resistance derived from the SCN-resistant parental plant line, but is essentially free from other undesirable characteristics previously associated with the parental line.

It is an object of the invention to provide improved methods for mapping genomic loci in SCN-resistant soybean plant lines, these methods utilizing an inbred line of soybean cyst nematodes.

It is another object of the present invention to provide superior soybean plants and plant lines which exhibit SCN resistance and have desirable characteristics hereinbefore not associated with plants having SCN resistance.

It is also an object of the present invention to provide methods for determining whether SCN resistance is present, for example, in a soybean plant, soybean plant line, soybean seed or soybean seed lot, by analyzing a DNA sample from the soybean plant, plant line, seed or seed lot for the presence of one or more of the molecular markers described herein.

Additional objects, advantages and features of the present invention will be apparent from the detailed description herein.

DESCRIPTION OF THE PREFERRED EMBODIMENTS

Figure 1:
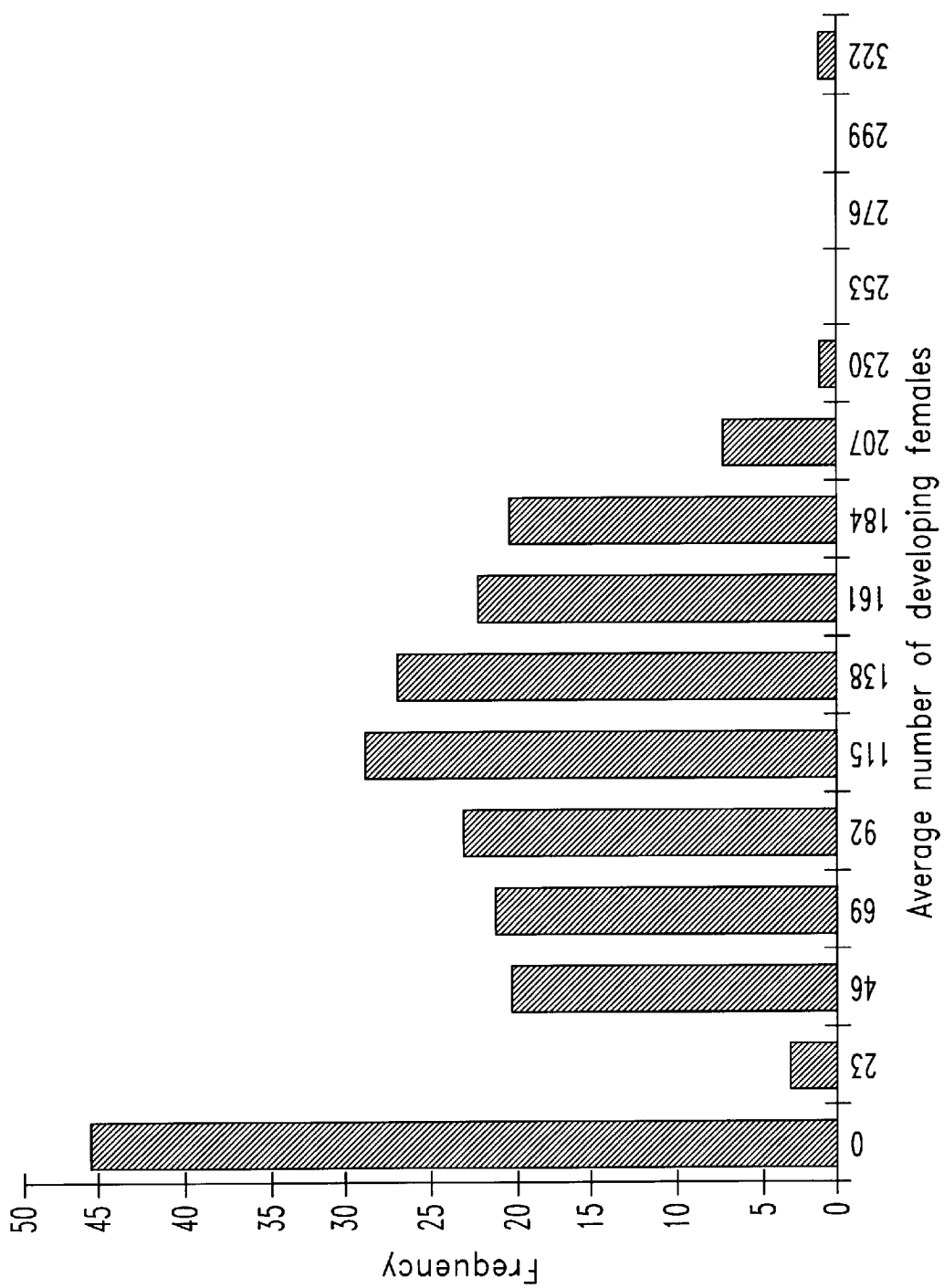
FIG. 1 is a histogram showing the mean frequencies of developed females per root system of F2:3 lines for the Hartwig×Williams 82 cross described in greater detail in Example 1.

For the purposes of promoting an understanding of the principles of the invention, reference will now be made to preferred embodiments thereof and specific language will be used to describe the same. It will nevertheless be understood that no limitation of the scope of the invention is thereby intended, such alterations and further modifications in the invention, and such further applications of the principles of the invention as described therein being contemplated as would normally occur to one skilled in the art to which the invention relates.

One novel aspect of the present invention involves the use of inbred soybean cyst nematodes to phenotypically screen plants for soybean cyst nematode ("SCN") resistance. Such a screening is useful, for example, in methods for mapping soybean genomic loci associated with SCN resistance. The use of inbred nematodes improves the quality of data collected as compared to using diverse field populations of SCNs. Another novel aspect of the invention relates to molecular markers, namely A006, A567, A487, A112, A096-A, A486 and B039, which the present inventors have shown to be linked to genomic loci associated with SCN resistance. A third novel aspect of the present invention involves a novel plant line, designated PUSCN14, which advantageously possesses SCN resistance genomic loci derived from Hartwig, and which is essentially free from the undesirable physical characteristics of Hartwig. Attempts to introgress SCN resistance from SCN-resistant descendants of PI437654 (such as, for example, Hartwig) into a plant line substantially free from these undesirable characteristics have heretofore proven unsatisfactory.

The novel use of inbred SCNs for mapping genomic loci associated with SCN resistance, and the novel use of the above-named molecular markers may be advantageously utilized in a wide variety of well-established mapping and breeding techniques. As such, the present invention provides novel SCN-resistant soybean plants and soybean lines, and improved methods for producing them utilizing inbred nematodes and the above-listed molecular markers in selective breeding techniques. In one aspect of the present invention, in general terms, SCN resistance is introgressed from an SCN-resistant parental soybean plant line (the "donor" soybean plant line) into an SCN susceptible parental soybean plant line (the "recipient" soybean plant line), which otherwise has desirable properties. In an inventive method, SCN resistance is introgressed by first mapping one or more molecular markers linked to one or more genomic loci associated with SCN resistance in the donor plant line, this mapping utilizing inbred soybean cyst nematodes for phenotypic screening and RFLP analysis for genotypic screening, examples of specific screening techniques being described more fully below.

According to another aspect of the present invention molecular markers, identified by the present inventors as being associated with SCN resistance, are used in restriction fragment length polymorphism ("RFLP") screening techniques that are now well-known in the art, to introgress SCN resistance from a donor plant line into a recipient plant line with minimal introgression of the poor physical traits characterized in, for example, Hartwig. Soybean plants and soybean lines developed according to the present invention advantageously derive a majority of their traits from a recipient parental plant line, and derive SCN resistance from the donor parental plant line. Although many have attempted to attain such a plant, the present inventors are the first to succeed in introgressing SCN resistance from a donor line into a recipient line to produce a recombinant plant line substantially free from undesirable traits such as, for example, viny stems (as opposed to erect), black seed coats (as opposed to clear) and low yield.

One starting material preferably used according to the present invention is a parental soybean plant from a plant line which is purebreeding for SCN resistance. As used herein, the term "purebreeding" may be used interchangeably with "true breeding" and is intended to refer to a plant line that is uniform and repeatable for a phenotype and/or a genotype. Preferably, the SCN-resistant parental line is a line that includes PI437654 in its pedigree. More preferably, the SCN-resistant parental line is Hartwig. In an alternate aspect of the invention, the SCN-resistant parental line is Peking. It is readily seen by one of ordinary skill in the art that other soybean plant lines that are purebreeding for SCN resistance are also useful in accordance with the present invention, a SCN-resistant soybean plant being readily obtainable.

Another starting material according to the present invention is a second parental soybean plant line which is non-resistant or less resistant to SCNs, a soybean plant of this type also being readily obtainable. A third starting material is one or more restriction enzymes, each useful for selectively cleaving DNA at a location having a specific nucleotide sequence, termed a "recognition site". Preferably, the restriction enzyme is one which recognizes a six nucleotide sequence. More preferably, the restriction enzyme is selected from the group consisting of Eco RI, Eco RV, Hind III, Xba I and Bgl II.

Also, DNA probes are used for restriction fragment length polymorphism ("RFLP") markers. Such probes can come from, for example, Pst I-cloned genomic libraries, and the cloned inserts used as probes may be amplified, for example by PCR, LCR, NASBA, or other amplification methods recognized in the art. Markers particularly useful in accordance with the present invention are the following: A006, A567, A487, A112, A096-A, A486 and B039. For RFLP mapping, restriction fragments are generated using specific restriction enzymes, and the digestion, electrophoresis, Southern transfers and nucleic acid hybridizations are conducted according to art-recognized techniques. See, e.g., Keim et al., Theor. Appl. Genet. 77:786–792, 1989, the disclosure of which is hereby incorporated herein by reference.

Another advantageous starting material for use in accordance with the present invention is an inbred line of soybean cyst nematodes. Inventive molecular marker identification methods utilizing inbred nematodes are superior to previously used methods because the genetic complexity and heterogeneity of SCN field populations have been obstacles in understanding the nature of soybean resistance to SCN. The use of advanced true inbred nematodes as inoculum in marker identification methods rather than heterogeneous field populations of SCNs allows a more accurate estimation of the genetic basis of resistance, thus allowing production of more reliable and accurate data.

In a preferred aspect of the present invention, the inbred nematodes are derived from at least about four generations of inbreeding. Inbreds may be advantageously isolated from a wide variety of SCN races and/or populations. As such, inbred SCNs of a wide variety of races and/or populations are contemplated for use in accordance with the present invention. The most preferred inbred SCN race is an inbred race-3 SCN, this race being perhaps the most common, and the most destructive, race presently known.

According to one aspect of the present invention, genomic loci associated with SCN resistance are mapped by identifying molecular markers linked to resistance loci, the mapping utilizing inbred SCNs for phenotypic scoring. The first step in a preferred method is to provide a plurality of F3 soybean plants derived by a first cross between a first SCN-resistant parental line and a second soybean plant line which is non-resistant or less resistant to SCNs, to yield a heterozygous F1 generation; self pollinating one or more plants from the F1 generation to yield a segregating F2 generation; and then self pollinating one or more plants from the F2 generation to produce F3 soybean plants.

This method further includes screening the plurality of F3 plants and plants from the parental lines for SCN resistance by introducing inbred SCNs onto seedling roots of the plants. Phenotypic screening may utilize well-known field screening and/or greenhouse screening techniques, specific examples of these techniques being described in greater detail below in the Examples. Both screening techniques preferably employ introducing inbred SCNs onto the roots of the selected plants when they are seedlings.

Also, this inventive method includes performing RFLP analysis of DNA samples isolated from F3 plants and from plants of each parental line with probes from the same plant species.

In one preferred manner of practicing the invention, a plant source (designated P1) having SCN resistance is recovered and crossed with a second plant (designated P2) that is SCN susceptible. Heterozygote plants from the F1 population are selfed to create a segregating F2 plant population which exhibits a gradient with respect to inbred SCN resistance.

Quantitative values for SCN resistance are determined by inbred SCN introduction, and assigned to each individual parent plant, F1 population plant, and F2 segregating plant and a genomic DNA sample from each plant is prepared for Southern blotting. Following preparation for Southern blot—which may be constructed to contain, for example, DNA from 25 to 50 or more different F2 plants—an RFLP probe is randomly chosen or selected from an RFLP genetic linkage map and hybridized to create the blot. Additional Southern blots are constructed using other RFLP probes. As indicated above, the RFLPs to be used for this purpose, i.e., the indirect selection of one or more SCN resistance QTLs, may but need not be randomly chosen. They can be selected in systematic fashion from the RFLP genetic linkage map. For example, for a trait of completely unknown location, several spaced RFLPs from each of the plant's genomic chromosomes may be selected for Southern blot testing for the location of DNA associated with the desired trait. Alternatively, of course, all mapped RFLPs may be used.

Finally, this method includes analyzing the data collected in the two previously-described steps to determine linkage between SCN resistance genomic loci and restriction fragment length polymorphism molecular markers. Following Southern blot procedures, a matrix may preferably be prepared having an identification of each plant that has been tested, followed by its quantitative trait measurement and the genotype as revealed by each RFLP probe tested. SCN resistance is preferably scored for these purposes by counting the number of developed females on the roots of each plant after a set amount of time. A specific example of a preferred scoring technique is described in detail in the Examples.

Typically, only three genotypes will be seen: P1, P2, and F1, the latter being heterozygous and having one chromosome from each parent. Thus, from the matrix, all plants can be grouped into one of three RFLP genotypic categories: P1P1, P1P2, or P2P2. If, with one or more RFLPs, the so-grouped plants, when averaged, all show approximately equal expression of the trait of interest, i.e., SCN resistance of plants in all groups is about the same, that RFLP is deemed noninformative. In other words, there was no association between the trait of interest and that particular RFLP. The genotype of the plant at the location of the RFLP was not relevant to the trait of interest.

Another RFLP, however, may show association with SCN resistance. With this information, it may be presumed that this RFLP, as revealed by the degree of its correlation to the P2P2 genotype, hybridizes to soybean DNA in the area of a gene for SCN resistance. In the above-described manner, it is possible to review results from a first group of RFLP probes used to screen for association to the trait of interest. Use of an RFLP genetic linkage map allows the selection of further RFLPs to be tested on an objective, rather than random, basis. Correlation may be improved by testing RFLPs located on either side of the RFLP or RFLPs which initially showed the strongest association. As is well known in the art, once the best probe or probes are identified, they may then be utilized, by way of example, in a breeding program to select plants having a desired height.

It is to be noted, of course, that in a multigenic system such as the SCN resistance system, there may be three, four, or more different genes contributing to one trait. In such a situation, there may, therefore, be many different quantitative expressions of that trait and no one gene can account for, or be relied upon to predict, that expression. The relative importance of each correlating RFLP can also be determined according to well-known practices. Particular values may be assigned to those RFLPs and utilized in a mathematical model to assist in predicting the degree of trait expression in a particular plant. In a preferred aspect of the present invention, data analysis is accomplished by performing multifactor analysis to identify molecular markers linked to SCN resistance genomic loci.

As is described in more detail in Examples 1 and 2, a preferred approach for mapping genomic SCN resistance loci is to detect statistically significant associations between molecular markers and the transformed mean of the number developed females found on the root systems. F2:3 lines are preferably used because they can be replicated. Since SCN resistance is conferred by more than one gene, using a replicated mapping population allows for the detecting of both major and minor effects. Stepwise regression, which is an improved version of the forward-selected procedure, has been recommended to be the best variable selection procedure. It has been concluded based on simulations that a forward selection of the phenotype on genetic markers can use the linkage disequilibrium created in a cross of inbred materials to identify significant associations.

Stepwise regression reexamines variables at every stage of regression using a partial F criterion compared with a preselected (P less than 0.01) percentage point of the appropriate F distribution. This allows for the judgement of the contribution of each variable as though it had been the most recent entry into the model. Thus, any variable that proves nonsignificant can be removed from the model though it may have been the best single variable at an earlier stage.

The mapping of SCN resistance genomic loci in Hartwig using a Hartwig×Williams 82 cross, described in greater detail in Example 1, showed that by using replicated progeny, both major and minor SCN resistance loci could be identified. The histogram shown in FIG. 1 shows bimodal distribution, with a peak at 0 and the remainder of the F2:3 lines show a normal distribution. In Hartwig, four unlinked RFLP markers showed significant effects on SCN resistance. As is shown in Table 1, marker A006 explained 91% of the total variation and probes A567, A487 and A112 each explained on additional 1% of the total variation.

TABLE 1

| Markers significantly (P < 0.01) associated with SCN resistance | | | | |
|---|---|---|---|---|
| Marker | Linkage group | $R^2$ | F | Prob > F |
| A006 | B | 0.91 | 1293.3 | 0.0001 |
| A567 | S | 0.01 | 17.5 | 0.0001 |
| A487 | A | 0.01 | 11.7 | 0.0008 |
| A112 | F | 0.01 | 10.2 | 0.0018 |

Comparison of the 3 genotypes of each individual marker showed that all markers had their lowest average of developed females in the HH class, with A006 having the lowest (See Table 2, below).

TABLE 2

Average number of developed females for $F_{2:3}$ genotypes of the four significant RFLP markers

| Markers | $HH^a$ | HW | WW |
|---|---|---|---|
| | Average number of developed females | | |
| A006 | 5 | 69 | 162 |
| A567 | 39 | 131 | 144 |
| A487 | 46 | 152 | 133 |
| A112 | 54 | 127 | 148 |

$^a$HH = Hartwig/Hartwig
HW = Hartwig/Williams 82
WW = Williams 82/Williams 82

Also, A006 was the only marker that showed a large decrease in females between the HW and WW genotypes. When analyzing genotypic combinations in this cross, as shown in Table 3, HH at all loci averaged 0 females, which was identical to parental Hartwig.

TABLE 3

Average number of developed females for combinations of $F_{2:3}$ genotypes of the four significant RFLP markers

| Markers | | | | |
|---|---|---|---|---|
| A006 | A567 | A487 | A112 | Developed females |
| $HH^a$ | HH | HH | HH | 0 |
| HH | WW | WW | WW or HW | 36 |

TABLE 3-continued

Average number of developed females for combinations of
$F_{2:3}$ genotypes of the four significant RFLP markers

| Markers | | | | |
|---|---|---|---|---|
| A006 | A567 | A487 | A112 | Developed females |
| WW | HH | HH | HH | 72 |
| WW | WW | WW | WW | 181 |

[a]HH = Hartwig/Hartwig
HW = Hartwig/Williams 82
WW = Williams 82/Williams 82

Lines with all WW genotypes averaged 181 females, which was very similar to Williams 82, which averaged 197 females. Lines that were HH at just the major locus (A006) and WW or HW at the other loci averaged 36 females, whereas WW at A006 and HH at the other loci averaged 72 females. The fact that only lines with HH genotypes at all four loci showed complete resistance indicates that all four loci are needed for complete resistance. Comparing the number of developed females with the individual locus or loci combinations showed there was an additive effect on the number of developing females.

Figure 2:
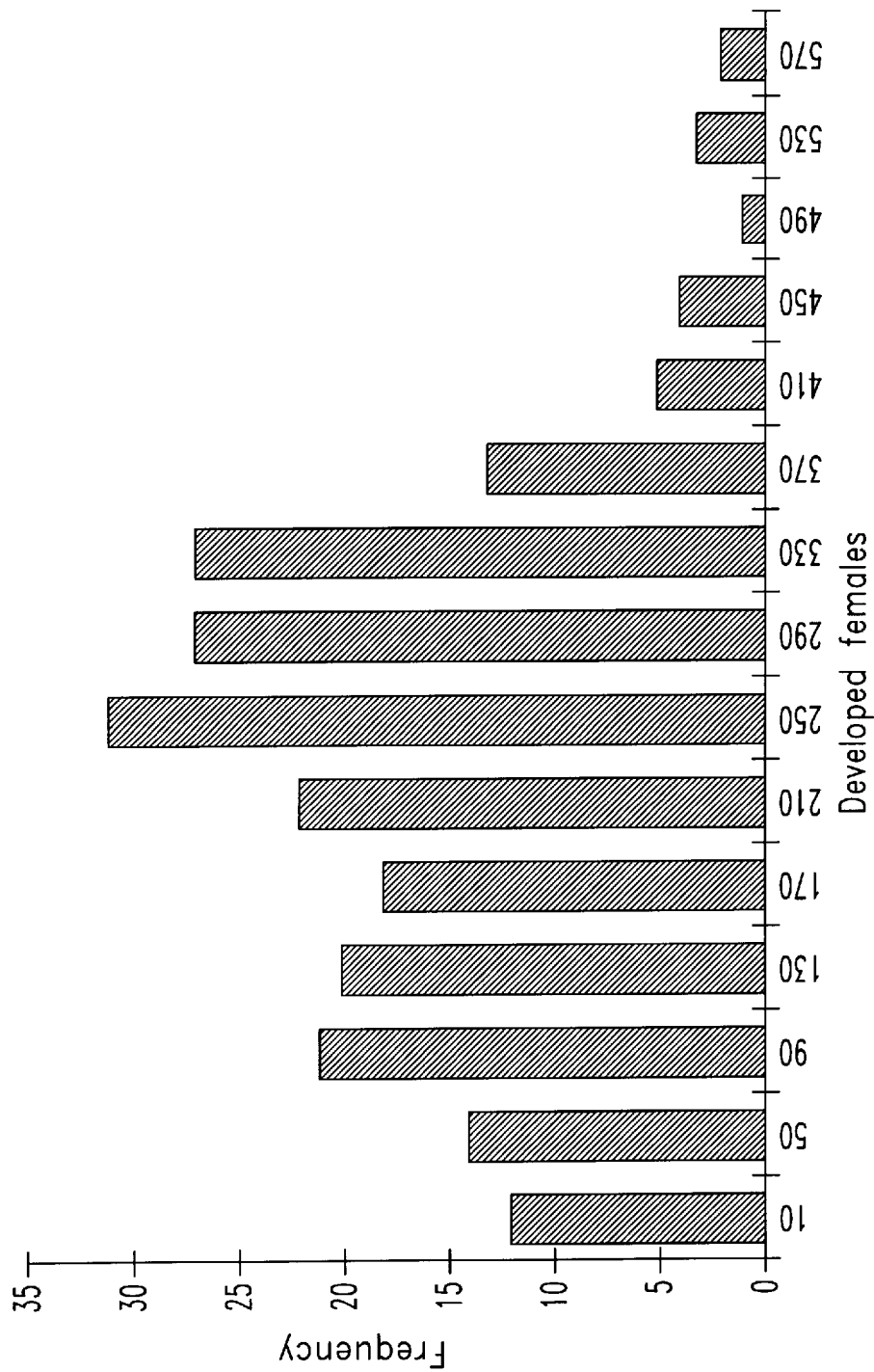
FIG. 2 is a histogram showing the mean frequencies of developed females per root system of F2:3 lines for the Peking×Williams 82 cross described in greater detail in Example 2.

With respect to the mapping of SCN resistance genomic loci in Peking, described in greater detail in Example 2, the histogram (FIG. 2) shows an approximately normal distribution. Four unlinked RFLP markers show significant effects on SCN resistance (See Table 4).

| Marker | Linkage group | R2 | F | Prob > F |
|---|---|---|---|---|
| A096-1 | A | 0.15 | 23.71 | 0.0001 |
| B039 | I | 0.03 | 6.14 | 0.0145 |
| A486 | A | 0.02 | 4.69 | 0.0321 |
| A112 | G | 0.02 | 4.45 | 0.0367 |

Figure 3:
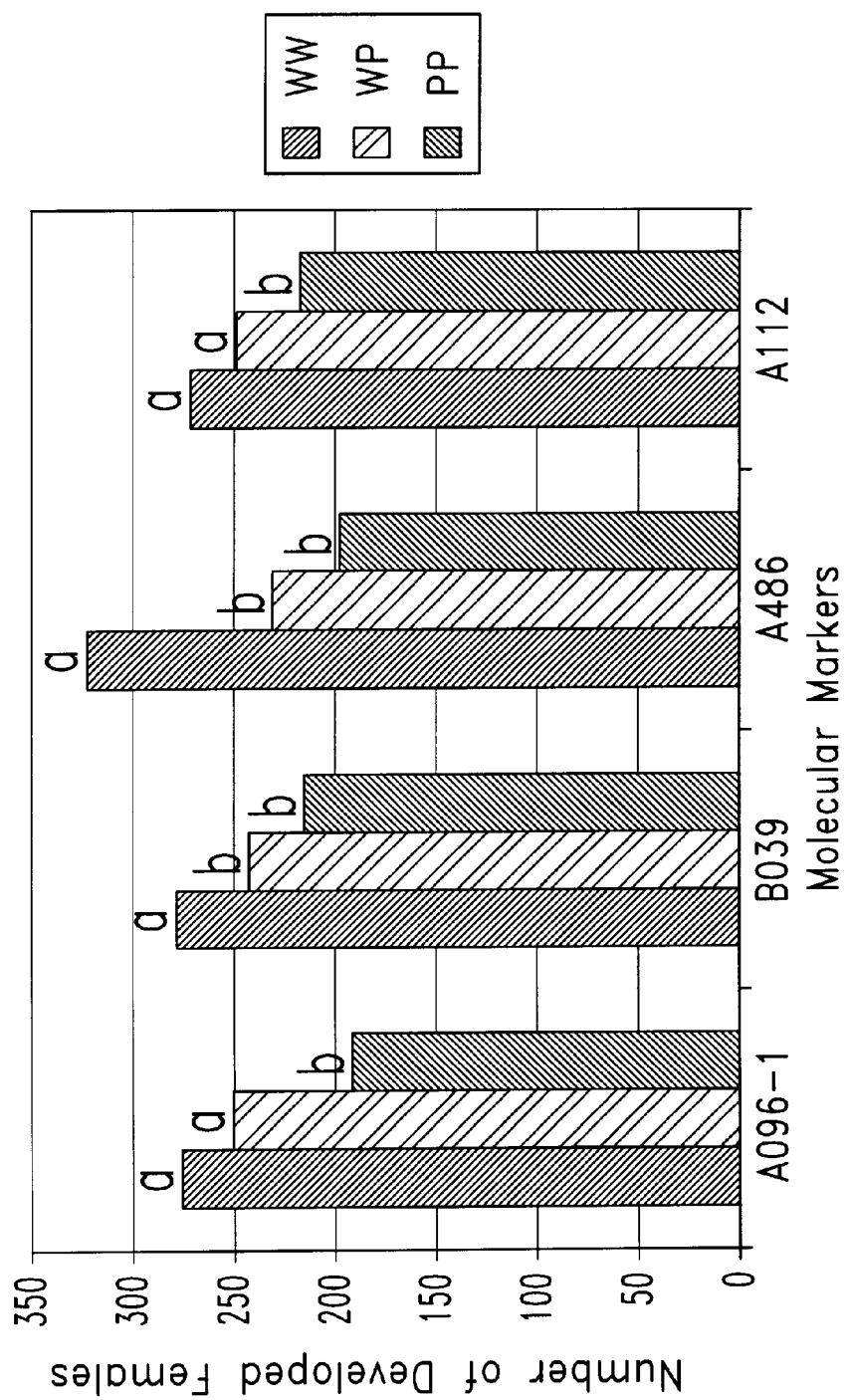
FIG. 3 is a histogram showing the average number of developed females for F2:3 genotypes of the four significant markers for the Peking×Williams 82 cross of Example 2. Bars within each marker group with the same letter were not significantly differing (P=0.001). WW=Williams 82/Williams 82; WP=Williams 82/Peking; and PP=Peking/Peking.

Comparison of the three genotypes of each individual marker showed that all markers had their lowest average of developed females in the homozygous Peking (PP) class (FIG. 3). At all four markers, the PP class had a significantly lower number of developed females than the homozygous Williams 82 (WW) class. No significant differences were found between the heterozygous class and PP class of markers A486 and B039. This would suggest that these resistance regions have a complete dominant effect.

According to another aspect of the present invention, there are provided methods for producing a superior new SCN-resistant recombinant soybean plant line substantially free from undesirable characteristics currently associated with SCN-resistant soybean lines. One preferred manner of producing such an improved soybean line first involves providing one or more plants from a parental soybean plant line which comprises in its genome one or more molecular markers selected from the group consisting of A006, A567, A487, A112, A096-A, A486 and B039. Preferably, the parental plant line is purebreeding for one or more of the molecular markers. More preferably, the parental plant line is purebreeding for the molecular marker A006; and even more preferably, the parental plant line is purebreeding for each of the following molecular markers: A006, A567, A487 and A112. In one preferred embodiment, the parental plant line is Hartwig.

The second step in this method comprises introgressing SCN resistance into a recipient soybean plant line which is non-resistant or less resistant to SCNs by performing marker assisted selection based upon the one or more aforesaid molecular markers.

In one preferred aspect of the invention, the introgressing is accomplished by first providing F2 plants by a first cross between an SCN parental plant line comprising one or more of the molecular markers and a plant line non-resistant or less resistant to SCNs to yield a heterozygous F1 generation; and self pollinating one or more plants from the F1 generation to yield a segregating F2 generation. Next, F2 plants, selected based upon the presence of one or more of the molecular markers are backcrossed with plants from the non-resistant parental soybean plant line to yield $BC_1F1$ generation plants. Then, $BC_1F1$ plants having the one or more molecular markers in their genome are selected as new SCN-resistant recombinant soybean plants.

Plants thus selected may then be used to develop new SCN-resistant recombinant soybean plant lines, for example, by single seed descent, or may optionally be further treated to selective breeding by performing additional backcrosses and selections, based upon the presence of one or more of the markers, for multiple generations. The presence of one or more of the markers may be readily determined by RFLP analysis of the plant's genomic DNA. Alternatively, a selected $BC_1F1$ plant may then be selfed, and additional selections performed based upon the presence of one or more of the molecular markers.

Also in a preferred method for producing a superior new SCN-resistant recombinant soybean plant line, F2 and/or $BC_1F1$ plants and/or their progeny are selected in each generation based upon not only the presence of the one or more molecular markers, inherited from the donor parent, but also based upon the presence of the least amount of non-SCN-associated DNA from the donor parent plant. As such, the majority of genomic DNA in plants selected for further breeding in this preferred method is inherited from a recipient soybean plant line parent, and selected plants thereby most closely resemble the plants from the recipient soybean plant line.

In an alternative preferred method for producing a superior new SCN-resistant recombinant soybean plant line, F2 and/or $BC_1F1$ plants and/or their progeny are selected in each generation based upon not only the presence of the one or more molecular markers, inherited from the donor parent, but also based upon the presence of one or more desirable traits from one or the other of the parental plant lines. For example, plants which have one or more of the aforesaid molecular markers in their genomes may preferably be screened for further breeding based upon the presence of an indeterminate growth pattern phenotype, this preferred method being described in more detail in the Examples.

In an alternate preferred method of producing a superior new SCN-resistant recombinant soybean plant line, such a plant line is developed by first mapping, or identifying, one or more molecular markers linked to one or more genomic loci associated with SCN resistance in a SCN-resistant plant line using RFLP analysis for genotypic screening and inbred SCN introduction for phenotypic screening. As is described more fully above, RFLP mapping typically includes developing a plant population segregating for the trait of SCN resistance, and selecting individual plants for phenotypic and genotypic screening and data collection.

The next step in this preferred method also comprises introgressing SCN resistance into a recipient soybean plant line which is non-resistant or less resistant to SCNs, the introgressing according to this method preferably being performed by marker assisted selection based upon one or more molecular markers identified in the first step using inbred SCNs as being linked to SCN resistance. A wide variety of advantageous methods may be employed to introgress resistance into a recipient plant line using markers thus identified, a few of these preferred methods being described above.

In regard to one aspect of the present invention, the present inventors have utilized inbred SCNs to map molecular markers in Hartwig, namely, A006, A567, A487 and A112. Further, through replicated progeny techniques based upon F2:3 families, the present inventors have developed a soybean plant line, namely PUSCN14, which possesses SCN resistance essentially free from other undesirable physical traits of Hartwig. PUSCN14, therefore, may be advantageously used as a donor plant line to introgress SCN resistance into a recipient plant line to yield a superior new recombinant plant line essentially free from the poor Hartwig traits. Seeds of soybean plant line PUSCN14 were deposited on Jan. 21, 1999 with American *Type Culture* Collection ("ATCC"), 10801 University Boulevard, Manassas, Va. 20110-2209. The ATCC accession number for this deposit is 203608.

The PUSCN14 soybean line may therefore be advantageously used according to the present invention to introgress SCN resistance into a wide variety of soybean varieties, including, for example, those currently being sold commercially and those currently under development. The superior ability of PUSCN14 to donate SCN resistance with minimal introgression of Hartwig's poor traits fills a long-felt need in the art of soybean breeding.

In a soybean breeding program, the methods of the present invention envision the use of marker-assisted selection utilizing the molecular markers described herein for one or more loci at a wide variety of population development stages in a two-parent population, multiple parent population, or a backcross population. Such populations are described in Fehr, W. R. 1987, *Breeding Methods for Cultivar Development;* and J. R. Wilcox (ed.) *Soybeans: Improvement, Production, and Uses,* 2d ed., the disclosures of which are hereby incorporated herein by reference.

Marker-assisted selection according to art-recognized methods may be made, for example, step-wise, whereby the different SCN resistance loci are selected in more than one generation; or, as an alternative example, simultaneously, whereby all loci are selected in the same generation. Marker-assisted selection for SCN resistance may be done before, in conjunction with, or after testing and selection for other traits such as seed yield, plant height, seed type, etc. For example, in one preferred aspect, plants are selected based upon the presence of SCN resistance molecular markers and the presence of indeterminant growth habits, this method being described in greater detail in the Examples.

The DNA from target populations, isolated for use in accordance with RFLP analysis, may be obtained from any plant part, and each DNA sample may represent the genotype of single or multiple plant individuals, including seed.

Marker-assisted selection may also be used to confirm previous selection for SCN resistance or susceptibility made by challenging plants with SCNs in the field or greenhouse and scoring the resulting phenotypes. Alternatively, plants can be analyzed by RFLP analysis to determine the presence of the above-described molecular markers, thus confirming the presence of a genomic locus associated with SCN resistance.

As such, also provided by the present invention are methods for determining the presence or absence of SCN resistance in a soybean plant, or alternatively in a soybean seed. These methods comprise analyzing genomic DNA from a plant or a seed for the presence of one or more of the following molecular markers: A006, A567, A487, A112, A096-A, A486 and B039. Preferably, the one or more molecular markers is selected from the group consisting of A006, A567, A487 and A112. According to this method, the analyzing comprises analyzing by restriction fragment length polymorphism analysis.

Another aspect of the present invention is a seed, a plant and/or a plant line which is produced according to the above described methods. The present invention relates to a recombinant SCN-resistant soybean plant, or alternatively a plant line, derived from selective breeding, which comprises first genomic DNA from a first soybean plant line, the first genomic DNA conferring SCN resistance to the recombinant soybean plant line; and second genomic DNA from a second soybean plant line, the second genomic DNA conferring other desired traits to the recombinant soybean plant line. According to this aspect of the invention, the first amount of genomic DNA comprises one or more molecular markers selected from the group consisting of A006, A567, A487, A112, A096-A, A486 and B039. More preferably, the one or more molecular markers is selected from the group consisting of A006, A567, A487 and A112. Most preferably, each of the above one or more molecular markers is present in the homozygous state. Also in a preferred recombinant soybean plant or plant line according to the present invention, the first genomic DNA comprises A006 in its homozygous state.

In a preferred aspect of the present invention, inventive recombinant, SCN-resistant plants are capable of producing, on average, greater than about 50 seeds per plant. Preferably, recombinant soybean plants and plant lines according to the present invention also comprise erect plants and, more preferably, have an average height of greater than about 25 cm. Additionally, recombinant soybean plants and plant lines are preferably capable of producing seeds, at least about 75% of said seeds having clear seed coats; and, more preferably, at least about 95% of said seeds have clear seed coats.

The invention will be further described with reference to the following specific Examples. It will be understood that these Examples are illustrative and not restrictive in nature.

EXAMPLE ONE

Identification of SCN Resistance Loci by Identifying Associated Molecular Markers: The Williams 82×Hartwig Cross Materials and Methods Plant materials Two-hundred F2:3 lines were derived from the cross 'Williams 82' (SCN-susceptible)×Hartwig (SCN-resistant). Hartwig was derived from the cross 'Forrest' ×PI 437654 and appears to have retained most of the resistance of PI 437654.

Nematode assay

F3 seedlings and parents were tested for SCN resistance using an SCN inbred developed from a race three wild type population as described in Example 3, below. The number of females developed on each root system was recorded. For each F2:3 line, phenotypes were determined from the transformed mean ($^{10}\log_{x+1}$) of four replications.

Molecular markers

A total of 211 RFLP markers and ten simple sequence repeats (SSR) were screened for polymorphism in the parental materials.

Data collection and analysis

DNA extraction, restricted digestion, blotting, and hybridization were done as described in Example 9, below. In brief, leaf tissue was harvested from F2:3 seedlings about 2 weeks after bulked seeds were germinated in pots containing vermiculite. Immediately after harvest, leaf tissue was freeze dried. DNA preparations were digested with either Eco RI, Eco RV, Hind III, Xba I or Bgl II. Restriction digested DNA from F2:3 families and both parental lines were separated on a 0.7% agarose gel, and Southern blotted to nylon membranes. RFLP probes were random primed with $^{32}$PdCTP and hybridized to Southern blots. Blots were then exposed to X-ray film and developed after the appropriate exposure time. SSR data were amplified by polymerase chain reaction according to known methods and amplified DNA fragments were separated on 4% acrylamide gels. Combined RFLP and SSR data were analyzed using MAPMAKER to generate a genetic linkage map of the probes. Each F2:3 family's genotype was identified by the alleles present at each molecular marker locus. Three states are possible at each locus, homozygous parent 1, homozygous parent 2 and heterozygous. Allele states and phenotypes were analyzed using stepwise regression and the model selection was made at P less than 0.01.

Results

Nematode screening

For parental material, the average number of females developed was 0 on Hartwig and 197 for Williams 82. Female counts on individual F3 plants ranged from 0 to 544 and average counts for F2:3 lines ranged from 0 to 345. F2:3 lines were divided into resistant, segregating and susceptible cells using the well-known Ward's minimum variance analysis. The mean number of females developed on resistant F2:3 lines were 0 and the mean on susceptible F2:3 lines was 163.

Molecular marker analysis

Fifty-three of the 211 RFLP markers and three of the 10 SSR were polymorphic between the parental material. These 56 molecular markers were screened using 200 F2:3 lines and used to construct a molecular marker linkage map. The linkage map consisted of 18 groups and 725 map units. The placement of markers to linkage groups was consistent with previously published probe locations (Shoemaker R C, Olson T C (1993) Molecular linkage map of soybean. In: Genetics maps sixth Ed, book 6 plants, Cold Spring Harbor Press, Cold Spring Harbor, pp. 131–138).

Markers associated with SCN resistance

Four unlinked RFLP markers were statistically significant and associated with SCN resistance (Table 1). The model coefficient of determination ($R^2$) was 94% and the partial $R^2$ of marker A006 (91%) accounted for most of the model $R^2$. Markers A567, A487 and A112 each contributed an additional 1% to the model $R^2$.

The means are shown in Table 2 of females developed for the genotypic classes of each individual marker, regardless of the genotype of the other significant markers. For each marker, the average number of developed females was lowest in the homozygous Hartwig (HH) genotypic class (Table 2). A006 was the only marker that showed an appreciable decrease of females when in a heterozygous state.

Examination of the genotypic combinations of all four markers showed F2:3 lines that were HH at all loci averaged 0 developed females, which is identical to the parental line Hartwig (Table 3). F2:3 lines that were WW at all four loci averaged 181 developed females which is similar to Williams 82. Averages of developed females on F2:3 lines with various combinations of HH and WW allele states ranged between the parental average.

EXAMPLE TWO

Identification of SCN Resistance Loci by Identification Association Molecular Markers: The Williams 82×Peking Cross Materials and Methods Plant materials Two-hundred F2:3 lines were derived from the cross 'Williams 82' (susceptible) X Peking (resistant).

Nematode assay

F3 seedlings and parents were tested for SCN resistance using an SCN inbred developed from a race-3 wild type SCN population as previously described. This inbred nematode was the same inbred used in the mapping of SCN resistance loci from Hartwig, as described in Example 1. The number of females developed on individual root systems was recorded. For each F2:3 line, phenotypes were determined from the transformed means ($^{10}\log_{x+1}$) of four to six replications.

Molecular markers

Parental cultivars were screened for polymorphism using 160 RFLP probes and 24 simple sequences repeats (SSR). A total of 49 polymorphic RFLP probes and 12 polymorphic SSR were used to screen the F2:3 materials. DNA preparations from bulked F2:3 seedlings were digested with either Eco RI, Eco RV, Hind III, or Xba I, separated on a 0.7% agarose gel, and probed with 32P labeled insert DNA. SSR data were amplified and separated on 4% acrylamide gels. Combined RFLP and SSR data were analyzed using MAPMAKER. Allele states and phenotypes were analyzed using stepwise regression and the model selection was made at P less than 0.001.

Results

Nematode screening

For parental material, the average number of females developed was 15 on Peking and 433 for Williams 82. Female counts on individual Peking plants ranged from 0 to 58 and from 110 to 688 on individual Williams 82 plants. Female counts on individual F3 plants ranged from 0 to 1320 and average counts for F2:3 lines ranged from 20 to 699.

Molecular marker analysis

Forty-nine of the 160 RFLP markers and 12 of the 24 SSR were polymorphic between the parental material. These 61 molecular markers were used to screen 200 F2:3 lines and to construct a molecular marker linkage map. The linkage map consisted on 18 groups and 556 total map units.

Markers associated with SCN resistance

Four unlinked RFLP, A096-A, A486, B039, and A112, markers were statistically significant and associated with SCN resistance and the model coefficient of determination (R2) was 22% (Table 4). The partial coefficients of determination were 15%, 2%, 3% and 2%, respectively. The four unlinked markers were on linkage groups A, G and I, with two markers on group A.

FIG. 3 shows the means of females developed for the genotypic classes of each individual marker, regardless of the genotype of the other significant markers. For each marker, the average number of developed females was lowest in the homozygous Peking (PP) genotypic class.

EXAMPLE THREE

Making, Maintaining and Using Inbred Soybean Cyst Nematodes

Materials and Methods

Nematode inbred

A true SCN inbred, obtained by sib-mating, was developed on the susceptible soybean cv. Essex from a race 3 wild-type population from a South Carolina soybean field. Subsequently, the inbred was advanced to the F4 generation (fourth sib-mating cross) at Purdue University. Each generation of inbreeding was carried out using 128 cavity seedling trays (cavity size 3×3×4.5 cm) filled with a 3 sand: 1 soil mix. Two randomly chosen second-stage juveniles (J2) hatched from cysts were placed near the root of a 4-day-old seedling in a new cavity. The soybean plants were pruned periodically to minimize growth and reduce water use. After 3 months, plants were examined for presence of females on the roots, and a success rate of 1–3% was obtained. Each infested plant was transplanted into a clay pot 10 cm in diameter (3 sand: 1 soil mix) along with new plants to increase the population. The inbreeding step was repeated three more times. At the F4 generation, cysts were increased to provide inoculum for the phenotypic screening. A race test was performed with 'Williams 82' as the reference susceptible.

Plant crosses:

'Williams 82'×'Hartwig' (derived from 'Forrest×PI 437.654) crosses were made to produce hybrids from which about 100 F1 seeds were harvested. One third of these F1 seeds were planted in the greenhouse to produce F2 seeds. These seeds were bulked, and about 220 seeds were chosen randomly to produce F3 seeds. F3 seeds produced by each F2 plant were kept separate from the F3 seeds produced by other plants. F3 seeds for each plant comprise one F2:3 family. F2:3 material was advanced by single seed descent.

Phenotype evaluations:

Screening began with F2:3 families, with each test replicated four times. Replicates were started about 2 weeks apart. Inoculum was prepared freshly by dissolving cyst wall and gelatinous matrix with a 50% solution of commercial bleach (5.25% sodium hypochlorite) to release eggs. Inoculum density for each replication was adjusted to 3,000 eggs and J2.ml. For each replication, two seeds from each family were germinated in sterilized sand in a 5 cm diameter pot. The most vigorous 5-day-old seedling, one for each of the 220 F3 families, was placed in a 2.5 cm diameter×7.5 cm long glass tube containing 10 ml of water mixed with 1 ml of nematode inoculum. A sand-soil mix was added to cover the roots. Tubes were placed in a water bath designed to maintain a root zone temperature of 24° C., and the plants were allowed to grow for approximately 30 days. Plants were fertilized every 2 weeks with a 0.04% solution of 20-20-20 (NPK) fertilizer. At the end of this incubation period, each plant was washed out of its tube and developing females dislodged with a jet of water. The number of females developing on the root system was recorded. Each seedling was then replanted in a 15 cm diameter pot and grown to produce F4 seeds. A total of 183 F2 and 17 F1 seedlings were screened in the same fashion. Resistant and susceptible parents were included in each test.

Analysis:

Numbers of females developing on roots were standardized using a log 10 (x divided by 1) transformation and then subjected to SAS Ward's minimum variance cluster analysis. Data for the F3 families were separated into cells of resistant, segregating, and susceptible phenotypes. Data for F2 plants were assigned to either resistant or susceptible cells. Goodness of fit with appropriate genetic ratios was tested using chi-square.

Results

In the race screening test, the nematode inbred used for this study behaved as a race 3 population. Indices of parasitism, defined as: [number of cysts developed on test differential/number of cysts on 'Williams 82']×100 for PI88.788, PI90.763, 'Peking,' and 'Pickett 71' were 3.9%, 0.4%, 2.5%, and 6.1%, respectively.

Numbers of developing females on individual F3 plants ranged from 0 to 544. Average counts from four replications from each F3 family ranged from 0 to 345. When Ward's minimum variance cluster analysis was used to assign means of transformed F3 family data to one of three classes, the algorithm placed 12 families in the resistant cell, 99 in the segregating cell, and 109 in the susceptible cell. This 12:99:109 observation was tested for deviation from the two- and three-gene expected ratios. Chi-square analysis indicated that the observed ratio was not significantly different from the expected ratio for a two-gene system (Table 5).

|  | Number or plants of families | | | | | | | | |
|---|---|---|---|---|---|---|---|---|---|
|  | Observed | | | Expected | | | Hypothesized | | |
| Generation | R | Seg | S | R | Seg | S | genes | Ratio | $X^2$ |
| $F_1$ | 0 | — | 17 | 0 | — | 17 |  | 0:1 | — |
| $F_2$ | 34 | — | 149 | 11 | — | 172 | rhg, rhg | 1:15 | 51.2 |
|  |  |  |  | 41 | — | 142 | Rhg, rhg | 3:13 | 1.5* |
| $F_3$ | 12 | 99 | 109 | 14 | 110 | 96 | 2 genes | 1:8:7 | 3.2* |
|  |  |  |  | 3 | 89 | 128 | 3 genes | 1:26:37 | 30.9 |

R = Resistant,
Seg = Segregating,
S = Susceptible.
*= Not significantly different from the expected ratio ($\alpha$ = 0.03).

All 12 families within the resistance cell averaged 0 cyst. Within the segregating and susceptible cells, the average number of cysts per family ranged from 0.3 to 110 and from 111 to 345, respectively.

All 17 F1 plants produced a susceptible response. Ward's minimum variance cluster analysis divided the 183 F2 plants into resistant and susceptible cells containing 34 to 149 plants, respectively (See Table 5). The 34:149 observed ratio was tested for deviation from the ratios of several two-gene systems and was not significantly different from a single dominant and single recessive genetic model (See Table 5).

EXAMPLE FOUR

Introgressing SCN Resistance into a Non-Resistant or Less Resistant Soybean Plant Line from Hartwig—Single Seed Descent Williams 82 was crossed with Hartwig. The seed was planted in the field and the resulting seed (F2) planted in the greenhouse and the resulting seeds (F3) harvested while keeping separate the seeds from each plant. A random F3 seed from each of 230 plants was planted and the resulting F4 seed harvested. The seeds from each individual plant were again kept separate. A random F4 seed from each of the 230 plants was planted and the resulting F5 seed harvested. This was repeated until F7 seed was harvested and identified as an inbred line. At each generation beginning with the F3 generation, plants were screened with inbred soybean cyst nematodes, and plants were selected for advancement based upon the presence of SCN resistance and other phenotypic characteristics subjectively determined to resemble Williams 82. Alternatively, plants are screened for the presence of one or more of the molecular markers listed herein using RFLP analysis and selected for advancement based upon the presence of one or more of the markers and other phenotypic characteristics subjectively determined to resemble Williams 82.

EXAMPLE FIVE

Introgressing SCN Resistance into a Newly-Developed Soybean Plant Line—Pedigree Method Using the SCN resistant recombinant inbred line, produced as described in Example 3, as a donor source, the SCN resistant trait is introgressed into other germ plasm sources. To develop new germ plasm, the SCN resistant recombinant inbred line is used as one of the parents. The resulting progenies are evaluated and selected at various locations for a variety of traits, including SCN resistance. SCN resistance is determined by phenotypic screening or by RFLP selection based upon the presence of the molecular markers listed herein.

EXAMPLE SIX

Introgressing SCN Resistance into a Recipient Soybean Plant Line—Backcrossing

Using the SCN resistant recombinant inbred line, produced as described in Example 4, as a donor source, the SCN resistant trait is introgressed into other soybean plant lines. A cross, using the SCN resistant recombinant inbred line as a parent, is made. The resulting plants are crossed back to the recipient soybean plant line that is being converted to SCN resistance. This crossing back to the parental line that is being converted may be repeated several times. After each round of backcrossing, plants are selected for SCN resistance, which can be determined by either phenotypic screening or by the selection of molecular markers linked to SCN resistance loci. Besides selecting for SCN resistance, the plants are also selected that most closely resemble the original plant line being converted to SCN resistance. This selection for the original plant line is done phenotypically or with molecular markers.

In one specific preferred method, $BC_NF1$ plants are genotypically screened for the presence of one or more markers linked to SCN resistance genomic loci. As used herein, the term "$BC_NF1$ plant" is intended to refer to a plant in the first generation after a specific backcross event, the specific backcross event being designated by the term "N", irrespective of the number of previous backcross events employed to produce the plant. Plants having the one or more markers present may preferably be backcrossed with plants of the parental line or, alternatively, be selfed, the plants resulting from either of these events also being genotypically screened for the presence of one or more markers linked to SCN resistance genomic loci. This procedure may be repeated several times.

In another specific preferred method, $BC_NF1$ plants are selfed to produce $BC_NF2$ seeds. $BC_NF2$ plants are then screened either genotypically using RFLP analysis, or phenotypically using introduction of inbred SCNs. Those plants having present one or more molecular markers linked to SCN resistance, or those plants displaying resistance, depending upon the screening method used, are backcrossed with plants of the parental line to produce $BC_NF3$ seeds and plants. This procedure may be repeated several times.

EXAMPLE SEVEN

Phenotypic Screening Techniques for Assessing Nematode Resistance—Field Procedure In the spring, infested fields, in which a susceptible cultivar has been grown for at least 1 year, are planted with potentially resistant entries and a highly susceptible cultivar, in alternating resistant and susceptible rows, or test strips. After 4 to 8 weeks of growth, random plants from the susceptible rows are carefully dug up, and soil removed from the roots by placing the soil ball in a bucket of water. Exposed roots are then examined for the presence of developing cysts. When nematodes are found on roots of susceptible plants, roots of the plants being screened for resistance are examined for the presence of developing cysts. Plants without observable cysts on their roots are considered resistant.

EXAMPLE EIGHT

Phenotypic Screening Techniques for Assessing Nematode Resistance—Greenhouse Procedure As is well known in the art, to extend screening time into winter, soil from infested fields is brought into a greenhouse. The suggested population level for good screening is 15 cysts per 250 cc of soil. If lower than this, a highly susceptible variety should be grown in the soil to increase the population level. Large bins are filled with this soil, and both resistant and susceptible plants are grown. The roots of each plant are examined for developing cysts as in the field procedure described in Example 7. To speed up the examination process, and to make it easier to detect developing cysts on roots, infested field soil is thoroughly mixed to obtain even distribution of inoculum. The screening is then carried out in small clay pots filled with infested soil, one seed per pot. Again, some pots are planted with a susceptible cultivar. When roots are formed around the periphery of the soil ball, each plant is carefully knocked out of the pot and the exposed roots examined for development of cysts. Using this technique, plant roots are examined more rapidly than is possible when roots have to be carefully dug out of soil.

EXAMPLE NINE

Scoring SCN Resistance Phenotypically

To obtain phenotypic data for scoring SCN resistance, the contents of a test tube or pot wherein a test plant is being grown are poured into a 4 quart bucket. Next, the soil is roiled with pressurized water until the liquid level reaches about one inch from the rim of the bucket, and the roiled water is poured over nested 25 and 60 mesh sieves. This is repeated until the roots of the plant are substantially clean. Next, the cyst material collected on the 60 mesh sieve is washed into a 50 ml beaker. The contents of the beaker are roiled and poured onto a 90 mm×90 mm counting chamber which has a cloth bottom marked with lines 10 mm apart. Then the chamber is placed over a porcelain Buchner type funnel with a diameter of 140 mm, and standing water is removed by vacuum. The counting dish with debris is placed on a support and examined at 10× magnification with a dissecting microscope so that the number of cysts may be counted.

EXAMPLE TEN

Selection for Multiple Traits—SCN Resistance and Determinant/Indeterminant Growth $BC_1F1$ seeds were obtained by backcrossing a SCN-resistant plant line developed from the Hartwig mapping population to the susceptible parent Williams 82; the SCN resistant line exhibiting determinant growth habits and Williams 82 exhibiting indeterminant growth habits. The $BC_1F1$ seeds were planted and resulting $BC_1F1$ plants were phenotypically screened for SCN resistance using SCN inbreds and genotypically screened with RFLPs linked to SCN resistance loci. The $BC_1F1$ plants all displayed indeterminate growth habits. $BC_1F1$ plants were selfed and $BC_1F2$ seeds were harvested from $BC_1F1$ plants that were found to be SCN resistant. The $BC_1F2$ plants were likewise screened for SCN resistance and were also scored for growth habits. Plants that exhibited both SCN resistance and indeterminate growth habits were isolated and advanced for further development.

EXAMPLE ELEVEN

Genotypic Screening Techniques for Assessing Nematode Resistance

DNA is isolated from any plant tissue or seed by standard methods and digested with the appropriate restriction enzyme or enzymes. The DNA may advantageously be isolated from parental material, from individuals in a segregating population or in an inbred line. The appropriate restriction enzymes are those previously used to detect polymorphism between the parental lines and for associating RFLPs with resistance loci. Each RFLP that is significantly associated with SCN resistance may be isolated using a different restriction enzyme or may be isolated using the same restriction enzyme as other significantly associated RFLP markers. In accordance with the present invention, marker A006 is a product of Eco RV digestion; marker A567 is a product of Xba I digestion; marker A487 is a product of Eco RV digestion; marker A096-A is a product of Eco RI digestion; marker A486 is a product of Bgl II digestion; marker B039 is a product of Bgl II digestion; and marker A112 is a product of Hind III digestion.

Digested DNA is then separated by electrophoresis in agarose gels. DNA is transferred to nylon membranes by capillary, vacuum or other methods. The DNA is then cross-linked to the membrane by heating in an oven for 2 hours at 80° C. or exposing to ultraviolet light for 2 minutes. The membrane is prehybridized in standard prehybridization buffer and at the appropriate temperature, which is dependent on the RFLP probe. The significant RFLP probe is labeled with either radioactive or chemiluminescent labels. The labeled probe is added to hybridization buffer, which is then substituted for the prehybridization solution. The probe is hybridized to the blot for the appropriate time and at the appropriate temperature. After hybridization, the blot is washed to remove any unbound probe. The washed blot is then exposed to X-ray film and after the appropriate exposure time, the X-ray film is developed. The allele states are determined by comparison to the parental material. There are a total of 3 allele classes that are possible: homozygous parent one, homozygous parent two, or heterozygous. Depending upon the population being tested, all three or only one or two of the allele classes may be present.

Plants selected are those that have alleles present that are linked to SCN resistance. Some plants may be homozygous for the allele states linked to SCN resistance at all loci, or a combination of homozygous for the allele states linked to SCN resistance at a number of loci and heterozygous at the remaining loci. Plants that are heterozygous at all resistance loci can be advanced and selected for homozygosity in later generations. Plants that are homozygous for the allele states not linked to SCN resistance at a number of loci may be back crossed to the SCN-resistant source or to another recombinant plant that contains allele states linked to SCN resistance loci that are not present in the first plant.

What is claimed is:

1. A method for producing a recombinant soybean cyst nematode-resistant soybean plant line, comprising:

identifying one or more molecular markers in a soybean cyst nematode-resistant donor plant line selected from PUSCN14 deposited as ATCC accession No. 203608 and soybean cyst nematode-resistant progeny therefrom by restriction fragment length polymorphism analysis; the one or more molecular markers being linked to one or more quantitative trait loci associated with soybean cyst nematode resistance; and introgressing soybean cyst nematode resistance into a recipient soybean plant line which is non-resistant or less resistant to soybean cyst nematodes by performing marker assisted selection to provide a recombinant soybean line.

2. The method according to claim 1, wherein said identifying comprises:

providing a plurality of F3 soybean plants derived by a first cross between the soybean cyst nematode-resistant donor plant line and a recipient soybean plant line which is non-resistant or less resistant to soybean cyst nematodes, to yield a heterozygous F1 generation; self pollinating one or more plants from the F1 generation to yield a segregating F2 generation; and then self pollinating one or more plants from the F2 generation to produce F3 soybean plant families;

screening the plurality of F3 plants and plants from the donor plant line and the recipient plant line for soybean cyst nematode resistance by introducing inbred soybean cyst nematodes onto seedling roots of the F3 plants;

performing restriction fragment length polymorphism analysis of DNA samples isolated from F3 plants and from plants of the donor plant line and the recipient plant line with probes from the same plant species, the DNA samples having been cleaved by one or more selected restriction enzymes; and determining linkage between soybean cyst nematode resistance genomic loci and restriction fragment length polymorphism molecular markers by performing multifactor analysis to identify molecular markers mapping to soybean cyst nematode resistance genomic loci.

3. The method according to claim 1, wherein said introgressing comprises:

providing F2 plants derived from selective breeding, the selective breeding including a first cross between the donor plant line and the recipient soybean plant line to yield a heterozygous F1 generation; and self pollinating one or more plants from the F1 generation to yield a segregating F2 generation;

backcrossing F2 plants with plants from the recipient soybean plant line to yield BC$_1$F1 generation plants, the F2 plants having the one or more molecular markers in their genome;

identifying BC$_1$F1 plants having the one or more molecular markers in their genome.

4. The method according to claim 3, further comprising performing additional backcrosses and selections based upon the presence of one or more of the markers in each plant selected for backcrossing.

5. The method according to claim 3, further comprising selfing BC$_1$F1 plants and performing additional selections based upon the presence of one or more of the molecular markers.

6. The method according to claim 1, wherein the one or more molecular markers is selected from the group consisting of A006, A567, A487 and A112.

7. The method according to claim 1, wherein the molecular marker is A006.

8. The method according to claim 1, wherein the marker assisted selection comprises selecting plants for breeding based upon the presence of the molecular marker A006 in its homozygous state.

9. A recombinant soybean cyst nematode-resistant soybean plant line obtained according to the method of claim 1.

10. A method for determining the presence or absence of soybean cyst nematode resistance in a soybean plant or a soybean seed, comprising:

analyzing genomic DNA from a soybean plant or a soybean seed for the presence of a molecular marker linked to a quantitative trait locus associated with soybean cyst nematode resistance; wherein said molecular marker is A006.

11. The method according to claim 10, further comprising:

analyzing genomic DNA from the soybean plant or soybean seed for the presence of a second molecular marker linked to a quantitative trait locus associated with soybean cyst nematode resistance;

wherein the second molecular marker selected from the group consisting of A567, A487 and A112.

12. The method of claim 10, wherein said analyzing comprises analyzing by restriction fragment length polymorphism analysis; the restriction fragment length polymorphism analysis comprising a genotypic screening for the presence of the molecular marker.

13. A method for reliably and predictably introgressing soybean cyst nematode resistance from a soybean cyst nematode-resistant soybean line into a non-resistant or less resistant soybean line comprising selecting plants for breeding based upon the presence of a molecular marker, wherein the molecular marker is A006.

14. The method according to claim 13, wherein the soybean cyst nematode-resistant soybean line is P1437654 or a descendent thereof.

15. The method according to claim 13, wherein the soybean cyst nematode-resistant soybean line is Hartwig or a descendent thereof.

16. The method according to claim 13, wherein the presence or absence of A006 is determined by restriction fragment length polymorphism analysis.

17. A recombinant soybean plant line designated PUSCN14, deposited as ATCC accession number 203608, and progeny therefrom: wherein the progeny exhibit soybean cyst nematode resistance.

18. The method according to claim 1, wherein the donor plant line is resistant to race-3 soybean cyst nematode.

19. The method according to claim 1, wherein the donor plant line is resistant to a plurality of races of soybean cyst nematode.

20. The method according to claim 13, wherein said selecting comprises selecting plants for breeding based upon the presence of a first molecular marker and a second molecular marker, wherein the first molecular marker is A006, and wherein the second molecular marker is selected from the group consisting of A567, A487 and A112.

21. A method for determining the presence or absence of soybean cyst nematode resistance in a soybean plant or a soybean seed, comprising:

analyzing genomic DNA from a soybean plant or a soybean seed for the presence of a molecular marker linked to a quantitative trait locus associated with soybean cyst nematode resistance; wherein said molecular marker is A096-A.

22. The method according to claim 21, further comprising:

analyzing genomic DNA from the soybean plant or soybean seed for the presence of a second molecular marker linked to a quantitative trait locus associated with soybean cyst nematode resistance;

wherein the second molecular marker is selected from the group consisting of A112, A486 and B039.

23. The method of claim 21, wherein said analyzing comprises analyzing by restriction fragment length polymorphism analysis; the restriction fragment length polymorphism analysis comprising a genotypic screening for the presence of the molecular marker.

24. A method for reliably and predictably introgressing soybean cyst nematode resistance from a soybean cyst nematode-resistant soybean line into a non-resistant or less resistant soybean line comprising selecting plants for breeding based upon the presence of a molecular marker, wherein the molecular marker is A096-A.

25. The method according to claim 24, wherein said selecting comprises selecting plants for breeding based upon the presence of a first molecular marker and a second molecular marker, wherein the first molecular marker is A096-A, and wherein the second molecular marker is selected from the group consisting of A112, A486 and B039.

26. The method according to claim 24, wherein the soybean cyst nematode-resistant soybean line is Peking or a descendent thereof.

27. The method according to claim 24, wherein the presence or absence of A096-A is determined by restriction fragment length polymorphism analysis.

28. A method for producing a soybean cyst nematode-resistant soybean line having desired characteristics, comprising:

providing a first parental soybean line which is purebreeding for a molecular marker selected from the group consisting of A006 and A096-A, the molecular marker mapping to a genomic locus associated with soybean cyst nematode resistance; and introgressing soybean cyst nematode resistance into a nonresistant or less resistant soybean line by selecting progeny plants for further breeding based upon the presence of the molecular marker to provide a recombinant soybean line.

29. The method according to claim 28, wherein said introgressing comprises introgressing soybean cyst nematode resistance into a nonresistant or less resistant soybean line by selecting plants for breeding based upon the presence of the molecular marker and the presence of a desired characteristic to provide a recombinant soybean line; and wherein the desired characteristic is an indeterminant growth pattern.

30. The method according to claim 28, wherein said providing comprises providing a first parental soybean line which is purebreeding for a first molecular marker selected from the group consisting of A006 and A096-A, and a second molecular marker selected from the group consisting of A567, A487, A112, A486 and B039, the first and second molecular markers mapping to genomic loci associated with soybean cyst nematode resistance; and wherein said introgressing comprises introgressing soybean cyst nematode resistance into a nonresistant or less resistant soybean line having desired characteristics by selecting progeny plants for further breeding based upon the presence of the first and second molecular markers and the presence of a desired characteristic to provide a recombinant soybean line.

31. The method in accordance with claim 1, wherein the restriction fragment length polymorphism analysis comprises a comparison of phenotypic data to genotypic data; the phenotypic data being obtained by introducing inbred soybean cyst nematodes onto soybean plants.

* * * * *